US010288582B2

(12) United States Patent
Berney et al.

(10) Patent No.: US 10,288,582 B2
(45) Date of Patent: May 14, 2019

(54) INTEGRATED ION SENSING APPARATUS AND METHODS

(71) Applicant: Analog Devices Global, Hamilton (BM)

(72) Inventors: Helen Berney, Limerick (IE); William Allan Lane, Waterfall (IE); Patrick Martin McGuinness, Pallaskenry (IE); Thomas G. O'Dwyer, Arlington, MA (US)

(73) Assignee: Analog Devices Global, Hamilton (BM)

( * ) Notice: Subject to any disclaimer, the term of this patent is extended or adjusted under 35 U.S.C. 154(b) by 217 days.

(21) Appl. No.: 14/993,871

(22) Filed: Jan. 12, 2016

(65) Prior Publication Data

US 2017/0199148 A1   Jul. 13, 2017

(51) Int. Cl.
 *G01N 27/414*   (2006.01)

(52) U.S. Cl.
 CPC .................. *G01N 27/4148* (2013.01)

(58) Field of Classification Search
 CPC ........ G01L 21/30; G01N 27/62; G01N 27/64; H01J 41/00; H01J 41/02
 See application file for complete search history.

(56) References Cited

U.S. PATENT DOCUMENTS

| | | | |
|---|---|---|---|
| 3,709,813 A * | 1/1973 | Johnson | G01N 27/36 204/420 |
| 4,104,704 A * | 8/1978 | Weaver | H01G 9/0425 29/25.03 |
| 4,360,415 A | 11/1982 | Brezinski | |
| 4,980,043 A | 12/1990 | Tomita et al. | |
| 5,011,589 A * | 4/1991 | Amemiya | G01N 27/414 204/416 |
| 5,139,626 A * | 8/1992 | Yamaguchi | G01N 27/4035 204/294 |

(Continued)

FOREIGN PATENT DOCUMENTS

| | | |
|---|---|---|
| CN | 102636532 A | 8/2012 |
| CN | 106959330 | 7/2017 |

(Continued)

OTHER PUBLICATIONS

Kojima, Shimpey, et al., "Microanalysis System for $pO_2$, $pCo_2$, Stacked Modules", *IEEE Sensors Journal*, vol. 5, No. 5, (Oct. 2005), 1120-1127.

(Continued)

*Primary Examiner* — Tung X Nguyen
*Assistant Examiner* — Dominic Hawkins
(74) *Attorney, Agent, or Firm* — Schwegman Lundberg & Woessner, P.A.

(57) ABSTRACT

An integrated ion-sensitive probe is provided. In an example, an ion-sensitive probe can include a semiconductor substrate and a first passive electrode attached to the semiconductor substrate. The first passive electrode can be configured to contact a solution and to provide a first electrical voltage as function of a concentration of an ion within the solution. In certain examples, a passive reference electrode can be co-located on the semiconductor substrate. In some examples, processing electronics can be integrated on the semiconductor substrate.

20 Claims, 5 Drawing Sheets

(56) References Cited

U.S. PATENT DOCUMENTS

| | | | |
|---|---|---|---|
| 5,213,675 A * | 5/1993 | Yamaguchi | G01N 27/414 204/416 |
| 5,945,678 A * | 8/1999 | Yanagisawa | H01J 49/168 250/287 |
| 6,419,809 B1 | 7/2002 | Suzuki et al. | |
| 6,554,982 B1 * | 4/2003 | Shin | G01N 27/301 204/401 |
| 6,599,409 B1 | 7/2003 | Broadley et al. | |
| 7,122,794 B1 * | 10/2006 | Miller | H01J 49/0013 250/294 |
| 7,156,965 B1 * | 1/2007 | Li | B82Y 35/00 204/400 |
| 8,298,399 B2 * | 10/2012 | Marchand | G01N 33/182 205/702 |
| 8,390,083 B2 | 3/2013 | O'Donnell et al. | |
| 8,535,499 B2 | 9/2013 | Blauw et al. | |
| 8,779,532 B2 | 7/2014 | O'Donnell et al. | |
| 9,041,150 B2 | 5/2015 | O'Donnell et al. | |
| 9,267,915 B2 | 2/2016 | O'Donnell et al. | |
| 9,494,498 B2 | 11/2016 | Pamula et al. | |
| 9,513,246 B2 | 12/2016 | O'Donnell et al. | |
| 9,592,001 B2 | 3/2017 | Barcelo et al. | |
| 2002/0049389 A1 | 4/2002 | Abreu | |
| 2003/0112012 A1 * | 6/2003 | Mosley | G01N 27/4167 324/446 |
| 2003/0168354 A1 | 9/2003 | Broadley et al. | |
| 2006/0246490 A1 | 11/2006 | Anderson et al. | |
| 2007/0138027 A1 | 6/2007 | Dinsmoor et al. | |
| 2008/0286762 A1 * | 11/2008 | Miyahara | C12Q 1/6825 435/29 |
| 2011/0180406 A1 * | 7/2011 | Hirshberg | G01N 27/333 204/406 |
| 2014/0012114 A1 * | 1/2014 | Zevenbergen | A61B 5/14521 600/346 |
| 2014/0151549 A1 * | 6/2014 | Steiner | H01J 43/30 250/288 |
| 2014/0197042 A1 | 7/2014 | Zhang et al. | |
| 2014/0197842 A1 | 7/2014 | Mehringer | |
| 2014/0266231 A1 * | 9/2014 | Haramoto | G01N 27/70 324/464 |
| 2015/0177183 A1 * | 6/2015 | Bakker | G01N 27/3335 205/789 |
| 2016/0178572 A1 * | 6/2016 | Zevenbergen | G01N 27/413 205/789 |
| 2016/0263575 A1 | 9/2016 | Foster et al. | |
| 2016/0320326 A1 | 11/2016 | Zevenbergen et al. | |
| 2016/0327419 A1 | 11/2016 | Hellevang et al. | |

FOREIGN PATENT DOCUMENTS

| | | |
|---|---|---|
| DE | 102017100496 | 7/2017 |
| JP | 6326569 A | 2/1988 |
| JP | 2007-313594 A | 12/2007 |

OTHER PUBLICATIONS

Lan, Wen-Jie, et al., "Paper-Based Electroanalytical Devices with an Integrated, Stable Reference Electrode", Harvard University. [online]. [retrieved on Apr. 5, 2017]. retrieved from the Internet: <URL: https://dash.harvard.edu/bitstream/handle/1/12361278/36545720.pdf?sequence=1>, (2013), 32 pgs.

Růžička, Jaromir, et al., "Integrated Microconduits for Flow Analysis", *Analytics Chirnica Acta*, 161, (1984), 1-25.

Shinwari, M. Waleed, et al., "Microfabricated Reference Electrodes and their Biosensing Applications", *Sensors*, 10 (3), (2010), 45 pgs.

Kothari, Rohit, et al., "Direct Imprint Patterning of 2-D and 3-D Nanoparticle/Polymer Hybrid and Crystalline Metal Oxide Structures for Printed Optical, Electronic, and Energy Devices", *2016 6th Electronic System-Integration Technology Conference (ESTC)*, (2016), 2 pgs.

"Application Serial No. PCT/EP2018/062505, International Search Report dated Aug. 8, 2018", (Aug. 8, 2018), 6 pgs.

"Application Serial No. PCT/EP2018/062505, International Written Opinion dated Aug. 8, 2018", (Aug. 8, 2018), 10 pgs.

Nie, Chuan, et al., "An integrated 1-11, flex-microfluidic-Si chip device towards 16-26 sweat sensing applications", Sensors and Actuators B: Chemical: International Journal Devoted to Research and Development of Physical and Chemical Transducers, vol. 227, (2016), 11 pgs.

Sevenbergen, Marcel A. G., et al., "Electrochemical Sensing of Ethylene Employing a Thin Ionic-Liquid Layer", Analytical Chemistry, vol. 83, No. 16, (Aug. 15, 2011), 9 pgs.

Sevenbergen, Marcel A. G., et al., "Solid state pH and chloride sensor with microfluidic reference electrode", IEEE International Electron Devices Meeting (IEDM), (Dec. 2, 2016), 4 pgs.

"Chinese Application Serial No. 201710019458.5, Office Action dated Aug. 15, 2018", w/ English Translation, 24 pgs.

\* cited by examiner

INTEGRATED ION SENSING APPARATUS AND METHODS

BACKGROUND

Figure 1:
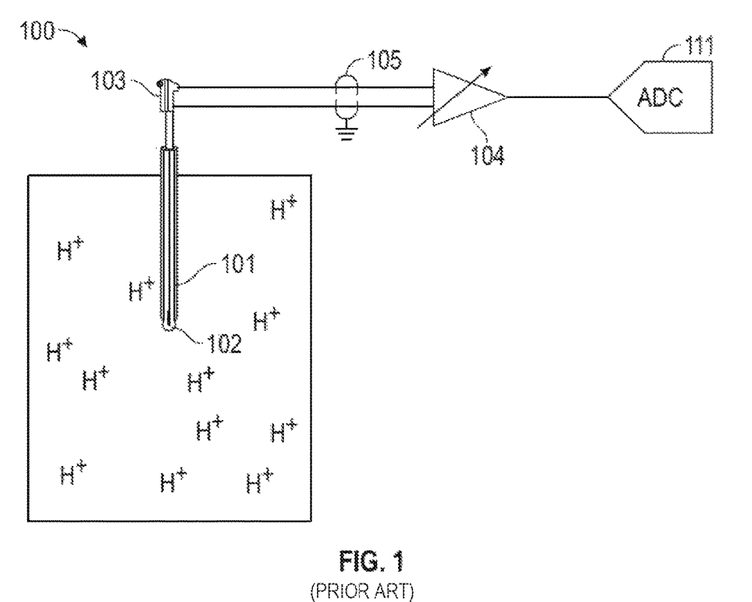
FIG. 1 illustrates generally a block diagram of a glass electrode system.

The classic 'gold standard' for measuring ion concentration is a glass electrode. A glass electrode system is a measurement device having a type of ion-selective, or ion-sensitive, electrode made of a doped glass membrane that is sensitive to a specific ion. FIG. 1 illustrates generally a block diagram of a glass electrode system 100. The glass electrode system 100 can include two electrodes, one for sensing the target ion 102, such as hydrogen ions ($H^+$), and one for providing a reference 101. In the example of FIG. 1, the two electrodes 101, 102 are located in liquids inside the glass electrode probe 103. Both electrodes 101, 102 provide a voltage at the interface to the liquid under test, the reference electrode 101 provides a nearly constant voltage which can be independent of the target ion concentration, and the sensing or indicating electrode 102 provides a voltage that varies with the concentration of the target ion. The voltages are conveyed via a wire medium 105 to an amplifier system 104 and then processed for display or data collection. In certain situations the voltages can be converted to digital values, via an analog-to digital converter (ADC) 111, for example, and further processed digitally. Characteristics of glass electrode systems that can interfere with measurements include output impedance on the order of 20 mega ohms ($M\Omega$) to 800 $M\Omega$, noise coupling to the wire medium 105 and expense of the wire medium and the probe 103. In addition to glass electrodes, there are low performance disposable solutions know as Litmus papers which are passive strips which change color in response to the concentration of a target ion. The litmus paper type measurements are not considered precision because, for example, using litmus papers is subject to a subjective reading of color, the papers themselves can interfere with small samples and it can be difficult to fabricate papers which cover full ion concentration ranges.

A relatively new solid state technology known as ion-sensitive, field effect transistor (ISFET) has emerged that is based on an activated FET gate, which can produce an output source-drain current related to the exponential of pH (Non-Nernstian). The technology has been used in DNA sequencing and food process control, but can have issues with charge trapping, hysteresis and drift that may have limited the technologies more widespread use. In addition, an ISFET provides an indicting electrode only, and an additional external reference electrode is usually required.

OVERVIEW

This document describes an integrated ion-sensitive probe. An integrated ion-sensitive probe is provided. In an example, an ion-sensitive probe can include a semiconductor substrate and a first passive electrode attached to the semiconductor substrate. The first passive electrode can be configured to contact a solution and to provide a first electrical voltage as function of a concentration of an ion within the solution. In certain examples, a passive reference electrode can be co-located on the semiconductor substrate. In some examples, processing electronics can be integrated on the semiconductor substrate.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present inventors have recognized that apparatuses and methods for a solid state ion-sensitive electrode and a system including a passive, solid-state, ion-sensitive electrode can offer a dramatic reduction in size and cost. In addition, compared to other solid state ion sensing solutions, examples of the present subject matter can provide reduced drift. In some examples, temperature sensing can be co-located with the ion sensing electrodes such as to provide an adjunct test that can assist in accurately reporting pH, for example. In such examples, the co-located electrodes and temperature sensor can have very low thermal mass, such that faster temperature equilibrium response can be provided, which may also help reduce temperature corruption of small samples. In certain examples, an amplifier system and memory can be co-located with the electrodes and can allow for factory or one-time field calibration of individual electrodes or sensors, which can be difficult in glass electrodes since the amplifier and sensor are not uniquely coupled. Finally, due to the much smaller size and cost, examples of the present subject matter can open up new markets which cannot presently use glass electrodes, such as, but not limited to, the prospect of high performance disposable ion sensing probes.

Figure 2:
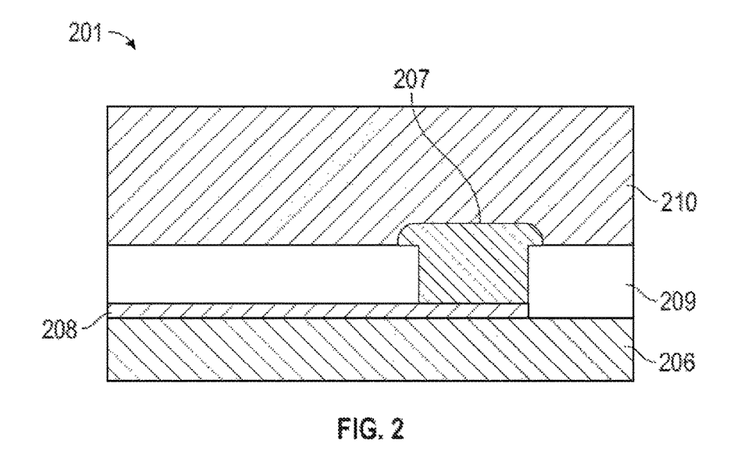
FIG. 2 illustrates generally an example of a passive, solid-state, ion-sensitive electrode 201.

FIG. 2 illustrates generally an example of a passive, solid-state, ion-sensitive electrode 201. The electrode 201 can include a portion of a substrate upon which an ion-sensitive material 207, a trace 208, and an insulator 209 can be integrally formed, such as using a semiconductor manufacturing process. In certain examples, the substrate can include a semiconductor substrate such as a silicon-based substrate 206. Other substrate materials can include, but are not limited to, glass or polymer substrates. By "passive" electrode 201, it is meant that the electrode 201—although integrated with a semiconductor substrate—is not integrated as part of a field-effect transistor (FET) or other transistor.

Thus, the electrode 201 is not part of a transistor gate region, transistor drain region, or transistor source region of a FET (although the electrode 201 may be fabricated on a substrate 206 that serves as a body terminal or region of a transistor). Therefore, because the electrode 201 is not part of a gate, source, or drain terminal or equivalent terminal of a transistor it can be regarded as a "passive" electrode—even though it may be interconnected (e.g., by an integrated semiconductor wiring trace) to an active transistor device, such as to a gate of a FET input device of an operational amplifier, or the like.

As part of a method of detecting an ion concentration of a solution, the ion-sensitive material 207 can be exposed to and can make contact with the solution sample 210. The ion-sensitive material 207 can attract or repel ions such that an electrical potential develops about the ion-sensitive material 207. The trace 208 can provide a low impedance conductor to provide or communicate the voltage to processing or sensing electronics or circuitry. The insulator 209 can provide a structure to allow the ion-sensitive material 207 to contact the trace 208 and to isolate the trace 208 from the sample solution 210. In certain examples, the ion-sensitive material 207 can include, but is not limited to, iridium oxide, silicon nitride, tantalum pentoxide, or other materials that are reactive to a target ion. In certain examples, the trace 208 can include, but is not limited to, gold, silver, platinum or other conductive material. In certain examples, the insulator 209 can include, but is not limited to, silicon oxide silicon nitride, polymer or other insulating material that is substantially impervious to liquid.

Figure 3:
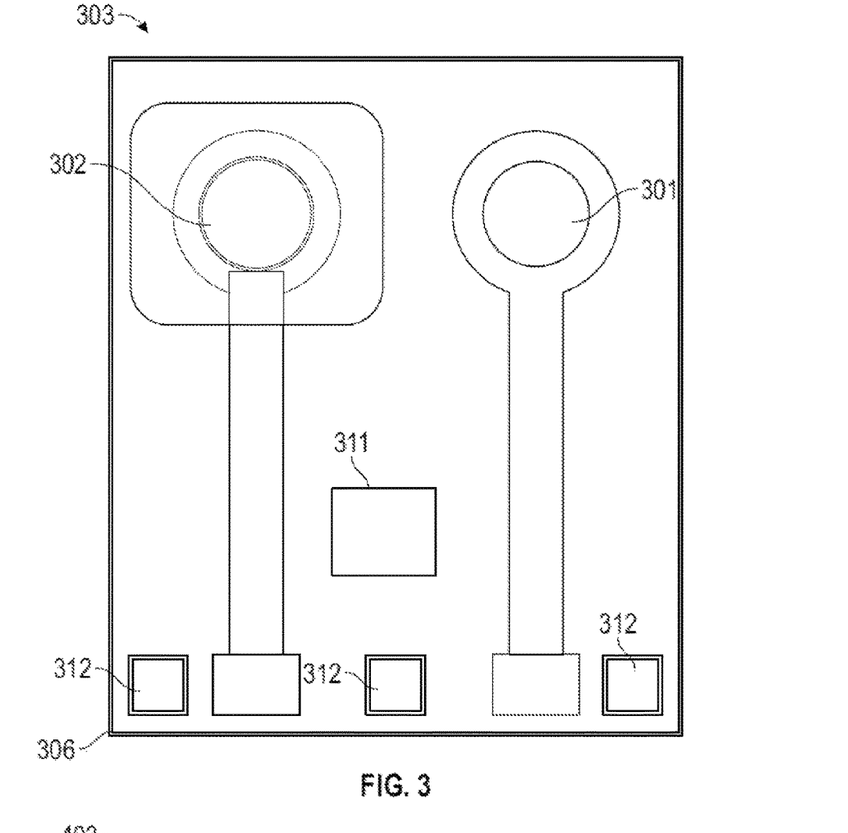
FIG. 3 illustrates generally an example of an integrated solid-state ion probe.

FIG. 3 illustrates generally an example of an integrated solid-state ion probe 303. In certain examples, the integrated solid-state ion probe 303 can include an indicating electrode 301, a reference electrode 302, integrated electronics 311, and a substrate 306 upon which each of the electrodes 301, 302 and the electronics 311 can be formed. In certain examples, the width and length of the integrated solid-state ion probe 303 can be on the order of 2 mm or less. In certain examples, the electronics 311 can include one or more amplifiers for receiving the signals provided by the electrodes 301, 302 and providing amplified signals to electronics coupled to connectors 312 of the probe. An advantage of an integrated solid-state ion probe 303 as illustrated in FIG. 3 is that the low-power or low-voltage signals provided by the electrodes 301, 302 can be processed or pre-processed with an amplifier co-located with the electrodes 301, 302. This can provide a distinct advantage over certain electronic probes in that the lead length of the conductors to the amplifier is orders of magnitude shorter in length. Smaller lead lengths reduce the susceptibility of the signals from the electrodes 301, 302 from being corrupted by electrical interference and also reduces the susceptibility to stray leakage currents. In certain examples, the electronics 311 can include an amplifier. In some examples, the electronics 311 can include an analog-to-digital converter. In some examples, the electronics 311 can include a wireless transmitter, a wireless receiver, or a combination thereof including a transceiver. In certain examples, the electronics 311 and/or terminations 312 of the integrated solid-state ion probe 303 can be sealed from contacting the solution sample being measured.

Figure 4:
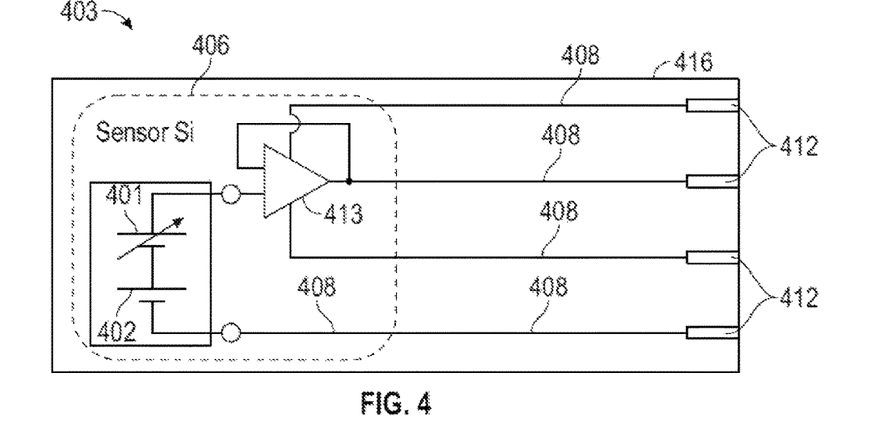
FIG. 4 illustrates generally a block diagram of an example of an ion probe.

FIG. 4 illustrates generally a block diagram of an example of an integrated solid-state ion probe 403. The integrated solid-state ion probe 403 can include a substrate 406 and/or a circuit board 416, or strip made of polymer or other material, including traces 408 and terminations 412 for a meter. The substrate 406 can include a reference electrode 402, an indicating electrode 401, and an amplifier 413. In certain examples, the indicating electrode 401 and the reference electrode 402 can be coupled in series between a reference voltage terminal and an input to the amplifier 413. The electrical connection between the indicating electrode and the reference electrode can be formed by the target solution during an ion concentration measurement of the target solution. In the illustrated example, the amplifier 413 can be in a voltage follower configuration. Such a configuration can provide a high impedance amplifier input to the sensed voltage of the electrodes 401, 402 and a low impedance output to efficiently convey the voltage to a meter device without as much risk of noise corruption as existing glass probes, for example. Other amplifier configurations integrated with the substrate 406 can be used. It is noted that having the amplifier or an amplifier system co-located with one or more electrodes 401, 402 of the integrated solid-state ion probe 403 can significantly reduce the output impedance of the integrated solid-state ion probe 403, such as compared to a glass electrode.

In addition, the integration of the electrodes 401, 402 with a substrate 406, individually or together, or the integration of one or more electrodes 401, 402 and an amplifier 413 or amplifier system on the substrate 406 can open up new uses for such an ion-sensitive probe. For example, the electrodes 401, 402 can be made relatively small, and can provide an accurate ion measurement using a very small solution sample size. In certain examples, the indicating electrode 401 can be formed at the bottom of a small volume vessel also integrated on the silicon substrate such that a drop of solution can be contained and can fully cover the indicating electrode 401 for measurement purposes. The small size format also allows the integrated solid-state ion probe 403 to be used in small areas. Such an integrated solid-state ion probe 403 can also provide accurate ion measurements when submerged in a large volume of solution. Other applications that an integrated solid-state ion probe 403 can make a reality is a disposable or semi-disposable probe. The passive electrode structure as discussed above, as well as the further integration of the reference electrode as discussed below, and the present knowledge of manufacturing integrating electronics can allow a probe to be manufactured consistently, in large numbers and at a fraction of the cost of other technologies. Such a probe could be regarded as a disposable probe or a single-use probe, in certain examples.

Figure 5A:
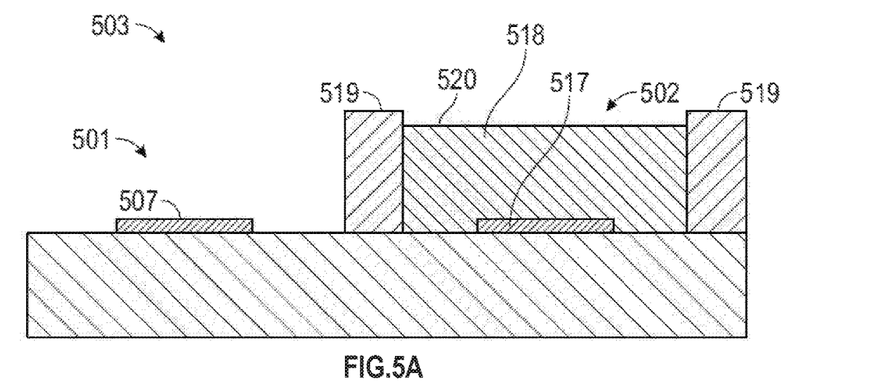
FIGS. 5A and 5B illustrate generally examples of configurations of a reference electrode.
Figure 5B:
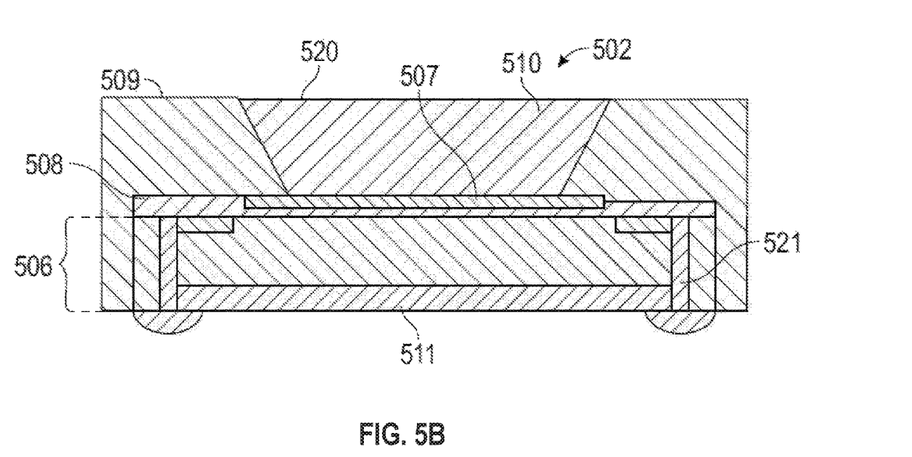

FIGS. 5A and 5B illustrate generally examples of configurations of a reference electrode 502. FIG. 5A illustrates generally a cross section of an example of an integrated solid-state ion probe 503 that includes an indicating electrode 501 and a reference electrode 502. The indicating electrode 501 includes a first ion sensitive material 507 that has an external surface that can contact a target solution. In certain examples, the reference electrode 502 has a second ion-sensitive material 517 that can be or is in contact with a reference material 518 having a known ion concentration such that the reference electrode 502 provides a reference or base voltage. The indicating electrode 501 is the electrode that is exposed to the material or solution for which and ion measurement is desired. The reference electrode 502 provides a reference or base voltage by having the second ion-sensitive material 517 contact a reference solution having a controlled ion concentration. In certain examples, the reference electrode 502 can include a containment barrier 519 surrounding an exposed surface of the second ion sensitive material 517. The containment barrier 519 can provide a vessel for the reference solution 518. In some examples, a top porous membrane 520 coupled to the top of the containment barrier 519 can provide a top barrier such that the reference solution 518 can be substantially sealed within a vessel that includes the second ion-sensitive material 517 of the reference electrode, the substrate 506 supporting the electrode, the containment barrier 519, and the top membrane 520. In some examples, the reference solution 518 can include a liquid. In some examples, the reference solution 518 can include a gel which can be easier to contain for extended periods. In certain examples, the reference electrode 502 can include the same ion sensitive material as used in the indicating electrode 501. In some examples, the second ion-sensitive material 517 of the reference electrode 502 is different than the first ion-sensitive material 507 of the indicating electrode 501. The probe relies on a liquid junction that allows ions to form an electrical connection between the indicating electrode 501 and the reference electrode 502. The liquid junction is an interface between the target solution and the reference solution 518 of the reference electrode 502. The channel or mechanism that allows contact between the reference solution 518 and the target solution can allow electrical conductivity between second ion-sensitive material 517 of the reference electrode 502 and the target solution. In certain examples, the channel or mechanism can include, but is not limited to, the porous membrane 520 or a micro-pore material, for example. In certain examples, the vessel formed by the containment barrier 519, and the top membrane 520 can entrap the reference solution 518 around the second ion-sensitive material 517 of the reference electrode 502 in order to ensure that there is a controlled environment around the second ion-sensitive material 517 and that the reference electrode 502 can generate a consistent voltage regardless of the characteristics of the target solution. In certain examples, the vessel can incorporate some type of porous junction that can allow ion flow between the target solution and the reference solution 518, and hence electrical connection, to the target solution, while at the same time minimizing fluid exchange across the junction.

FIG. 5B is another configuration of an example reference electrode 502. The reference electrode 502 includes a substrate 506, a first material 508 that is conductive such as gold, an ion-sensitive material 507, packaging material 509, and a reference material 510. In certain examples, the substrate 506 is a semiconductor substrate and the first material 508 provides traces to route electrical signals to different areas of the substrate 506. In certain examples, the packaging material 509 can protect the substrate 506 and the first material 508, and can provide a vessel for containing the reference material 510. In certain examples, the ion-sensitive material 507 of the reference electrode 502 can provide at least a portion of an interior surface of the vessel. In certain examples, the reference material 510 can be in gel form. In some examples, an upper membrane 520 can extend across the vessel and can couple to the packaging material 509 to seal the reference material 510 within the vessel formed by the packaging material 509, the ion-sensitive material 507 and the upper membrane 520. In some examples, the substrate 506 can include active electronics 511 such that signals from the reference electrode 502 can be processed as close as possible to the reference electrode 502. Such a design limits the length of conductive media from the reference electrode 502, and, in some cases, a co-located indicating electrode, that are exposed to potential interfering signals compared to a glass electrode. In some examples, the active electronics 511 can reside on a side of the substrate 506 opposite the ion-sensitive material 507 and signals can be routed to the active electronics 511 using through silicon vias (TSVs) 521.

Figure 6A:
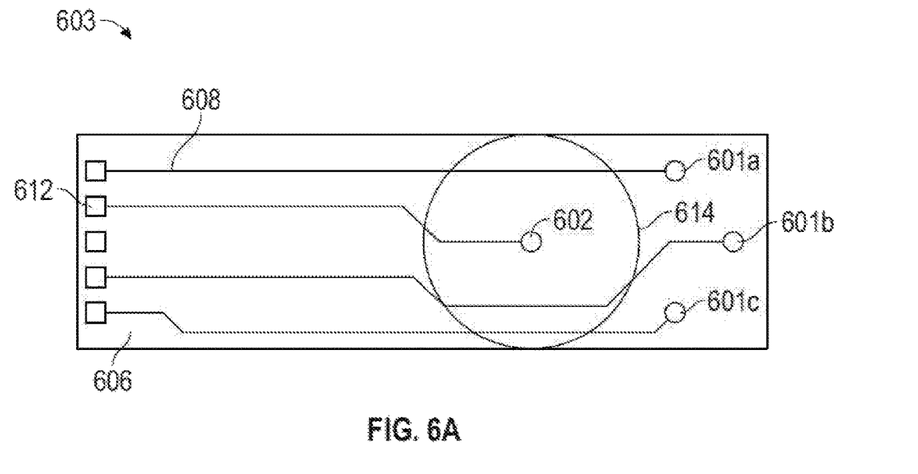
FIGS. 6A and 6B illustrate generally examples of probe layouts that include a reference electrode and one or more indicating electrodes.
Figure 6B:
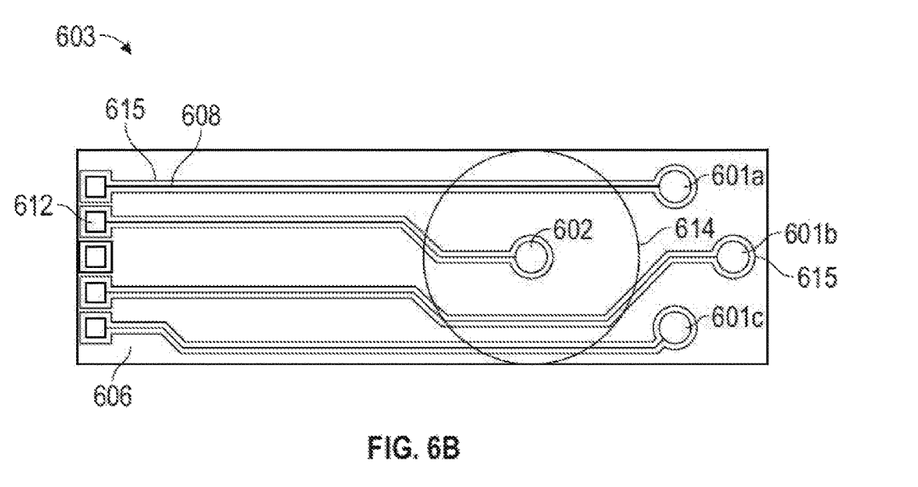

FIGS. 6A and 6B illustrate generally an example of probe layouts 603 that include a reference electrode 602 and one or more indicating electrodes 601. FIG. 6A illustrates generally an example of a probe layout 603 including a reference electrode 602 and three indicating electrodes 601a, 601b, 601c. Each electrode 601x, 602 is electrically connected to a trace 608 of a substrate 606 of the probe layout 603. Each trace 608 routes the voltage or signal of the electrode to a connector 612 of the substrate 606 or some other termination. In some examples, each trace 608 can route the voltage or signal to active electronics (not shown) integrated with the substrate 606. In some examples, each trace 608 can route the voltage or signal to active electronics integrated located on an opposite side of the substrate via a TSV. In certain examples, the active electronics can include an amplifier, for example, that can buffer or convert the signal received via the trace 608 and electrodes 601x, 602 to a more noise immune signal.

In certain examples, the reference electrode 602 can include a well to retain reference material. The probe layout 603 includes a circle 614 indicating a location of a containment barrier, for example, that can form a portion of the vessel. In certain examples, the diameter of the electrodes 601x, 602 can vary depending on a number of factors including anticipated environment the probe is designed to be used in. For example, if the probe is to be used for measuring very small samples, the electrodes may also be relatively small. In some examples, the electrodes, both reference 602 and indicating 601x can have diameters that range from 250 micrometers (um) to 1 millimeter (mm) or more. Good results have been attained with electrode diameters of 500 um and 300 um. In certain examples, the diameter of the containment barrier can be between 1 mm and 6 mm although other diameters are possible.

FIG. 6B illustrates generally an example probe layout 603 having a reference electrode 602 and three indicating electrodes 601a, 601b, 601c, each electrode having an electrode diameter of about 500 um. Each electrode 601x, 602 is coupled to a conductor or trace 608 of a substrate 606 of the probe layout 603. In addition, each trace 608 and each electrode 601x, 602 is surrounded by a shield trace 615 of the substrate 606. The shield trace 615 is typically coupled to a reference potential such as ground, for example. In some examples, each trace 608 and each electrode 601x, 602 can have individual shield traces 615 capable of being connected to individual potentials. Each shield trace 615 is designed to protect the electrode 601x, 602 and the electrode conductor or trace 608 from stray electrical interference by routing such interference to ground.

Figure 7:
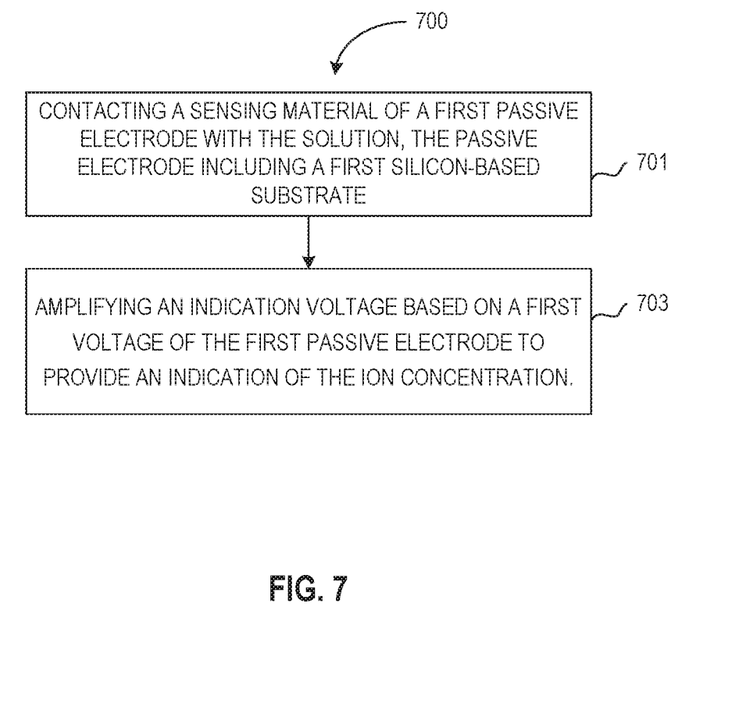
FIG. 7 illustrates generally an examples of a method of operating an ion-sensitive probe that includes a passive electrode integrated on a semiconductor substrate.

FIG. 7 illustrates generally an example method 700 of operating an ion-sensitive probe that includes a passive electrode integrated on a semiconductor substrate. At 701, a passive ion-sensitive probe integrated on a substrate can contact a solution. At 703, a first voltage of the first passive electrode can be amplified to provide an indicating voltage indicative of an ion concentration of the solution. In certain examples, the amplifier can be integrated on the silicon based substrate such that the output voltage of the amplifier is significantly more noise immune than the signal from the passive electrode. In some examples, a reference electrode can be located adjacent the passive electrode on the substrate.

VARIOUS NOTES & EXAMPLES

In Example 1, an ion-sensitive probe to measure the concentration of an ion within a solution can include a semiconductor substrate and a first passive electrode integrated with the semiconductor substrate and configured to contact the solution and to provide a first electrical voltage as a function of the concentration of an ion within the solution.

In Example 2, the probe of Example 1 optionally includes an amplifier having an input that is electrically coupled to the first passive electrode.

In Example 3, the amplifier of any one or more of Examples 1-2 optionally is integrated with the substrate.

In Example 4, the probe of any one or more of Examples 1-3 optionally include a containment barrier for the solution, wherein the solution is a reference solution, and the containment barrier is configured to maintain the reference solution in constant contact with the electrode.

In Example 5, the reference solution of any one or more of Examples 1-4 optionally is a gel.

In Example 6, the first passive electrode of any one or more of Examples 1-3 optionally includes a containment barrier and a first sensing material configured to provide the electrical voltage. The containment barrier optionally is attached to the semiconductor substrate and is configured to form a barrier around a location of contact between the solution and the sensing material. The containment barrier and the semiconductor substrate optionally are configured to form at least a portion of a slightly porous container for the reference solution.

In Example 7, the probe of any one or more of Examples 1-6 optionally includes a second passive electrode integrated with the substrate.

In Example 8, the second passive electrode of any one or more of Examples 1-7 optionally is configured to contact a reference solution.

In Example 9, the reference solution of any one or more of Examples 1-8 optionally includes a gel.

In Example 10, the probe of any one or more of Examples 1-9 optionally includes an amplifier electrically coupled to the first passive electrode and the second passive electrode.

In Example 11, the amplifier of any one or more of Examples 1-10 optionally is integrated with the substrate.

In Example 12, the first electrode of any one or more of Examples 1-11 optionally includes a first sensing material configured to generate the electrical voltage when in contact with the solution, and the first sensing material of any one or more of Examples 1-11 optionally includes iridium oxide configured to sense hydrogen ions.

In Example 13, the second electrode of any one or more of Examples 1-12 optionally includes a slightly porous containment barrier and a first sensing material configured to generate the electrical voltage. The containment barrier of any one or more of Examples 1-12 optionally is attached to the semiconductor substrate and is configured to form a ring around a point of contact between the solution and the sensing material. The containment barrier and the substrate form at least a portion of a container for the reference solution.

In Example 14, a diameter of a contact area of the first passive electrode of any one or more of Examples 1-13 optionally is from 250 micrometers (um) to 1 millimeter (mm).

In Example 15, the semiconductor substrate of any one or more of Examples 1-14 optionally includes a first trace coupled to the first passive electrode, the trace configured to communicate the electrical voltage to sensing circuitry.

In Example 16, the semiconductor substrate of any one or more of Examples 1-15 optionally includes a shield trace surrounding the first passive electrode and the first trace, the shield trace configured to shield the electrical voltage from noise.

In Example 17, a location of contact of the first passive electrode with the solution, of any one or more of Examples 1-3, optionally does not include a transistor configured to sense the ion.

In Example 18, a method for sensing an ion concentration of a solution can include contacting a sensing material of a first passive electrode with the solution, the first passive electrode including a first semiconductor substrate, and amplifying an indication voltage based on a first voltage of the first passive electrode to provide an indication of the ion concentration.

In Example 19, the method of any one or more of Examples 1-18 optionally includes contacting a sensing material of a second passive electrode with a reference solution, the second passive electrode including a second semiconductor substrate, and summing the first voltage of the first passive electrode with a second voltage of the second passive electrode to provide the indication voltage.

In Example 20, the first semiconductor substrate and the second semiconductor substrate of any one or more of Examples 1-19 optionally form a single substrate structure.

In Example 21, the amplifying an indication voltage of any one or more of Examples 1-20 optionally includes amplifying the indication voltage using an amplifier circuit integrated with the first semiconductor substrate.

In Example 22, an ion-sensitive probe to measure the concentration of an ion within a solution can include a semiconductor substrate, and a first passive electrode integrated with the semiconductor substrate and configured to contact the solution, a second passive electrode, integrated with the semiconductor substrate and configured to contact a reference solution having a specified concentration of the ion, an amplifier circuit, integrated with the same semiconductor substrate, and connected to the first and second passive electrodes, wherein the amplifier circuit is configured to provide a first electrical voltage as function of the concentration of an ion within the solution.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An ion-sensitive probe to measure a concentration of an ion within a solution, the ion-sensitive probe comprising:
   a semiconductor substrate;
   a first passive electrode integrated with the semiconductor substrate and configured to contact the solution and to provide a first electrical voltage as a function of the concentration of the ion within the solution;
   a second electrode integrated with the semiconductor substrate and configured to contact a reference solution, the second electrode in electrical contact with the first passive electrode; and
   an amplifier integrated with the semiconductor substrate and having an input electrically coupled with the first passive electrode, wherein a location of the amplifier integrated within the semiconductor substrate is configured to provide a co-integrated transmission path of the first voltage to reduce susceptibility of interference of the first voltage between the first electrode and the input of the amplifier.

2. The probe of claim 1, including a containment barrier for the reference solution, the containment barrier configured to maintain the reference solution in constant contact with the second electrode.

3. The probe of claim 2, wherein the reference solution is a gel.

4. The probe of claim 1, wherein the second electrode is a passive electrode.

5. The probe of claim 4, wherein the reference solution includes a gel.

6. The probe of claim 4, wherein the amplifier is electrically coupled to the first passive electrode and the second passive electrode.

7. The probe of claim 4, wherein the first electrode includes a first sensing material configured to generate the electrical voltage when in contact with the solution; and
   wherein the first sensing material includes iridium oxide configured to sense hydrogen ions.

8. The probe of claim 7, wherein the second electrode includes
   a containment barrier;
   a first sensing material configured to generate the electrical voltage;
   wherein the containment barrier is attached to the semiconductor substrate and forms a ring around a point of contact between the solution and the sensing material; and
   wherein the containment barrier and the semiconductor substrate form at least a portion of a container for the reference solution.

9. The probe of claim 1, wherein a diameter of a contact area of the first passive electrode is from 250 micrometers (um) to 1 millimeter (mm).

10. The probe of claim 1, wherein the semiconductor substrate includes a first trace coupled to the first passive electrode, the trace configured to communicate the electrical voltage to sensing circuitry.

11. The probe of claim 10, wherein the semiconductor substrate includes a shield trace surrounding the first passive electrode and the first trace, the shield trace configured to shield the electrical voltage from noise.

12. The probe of claim 1, wherein a location of contact of the first passive electrode with the solution does not include a transistor configured to sense the ion.

13. The ion-sensitive probe of claim 1, including:
   a plurality of third passive electrodes; and
   active electronics integrated with the semiconductor substrate, the active electronics configured to couple each of the plurality of third passive electrodes and the first passive electrode to the amplifier.

14. The ion-sensitive probe of claim 1, including a wireless transmitter configured to wirelessly transmit a digital representation of an output of the amplifier.

15. the ion-sensitive probe of claim 14, wherein the wireless transmitter is integrated with the semiconductor substrate.

16. A method for sensing an ion concentration of a solution, the method comprising:
   contacting a sensing material of a first passive electrode with the solution, the first passive electrode integrated in a semiconductor substrate;

contacting a sensing material of a second electrode with a reference solution, the second electrode integrated in the semiconductor substrate;

generating a sensing voltage via a series connection of the first passive electrode and the second electrode, the sensing voltage indicative of the ion concentration of the solution;

amplifying a voltage of the first passive electrode and a voltage of the second passive electrode to provide the sensing voltage; and wherein the amplifying a voltage of the first passive electrode and a voltage of the second passive electrode includes amplifying the voltage of the first passive electrode and the voltage of the second passive electrode using an amplifier circuit integrated with the semiconductor substrate, wherein a location of the amplifier integrated within the semiconductor substrate is configured to provide a co-integrated transmission path of the first voltage to reduce susceptibility of interference of the first voltage between the first electrode and the input of the amplifier.

17. The method of claim 16, wherein contacting a sensing material of a second electrode includes contacting a sensing material of a second passive electrode with a reference solution.

18. The method of claim 16, including communicating amplifier information from the ion-sensitive probe via a wireless transmitter.

19. The method of claim 16, including coupling one passive indicating electrode of an plurality of passive indicating electrodes to the amplifier, the array of passive indicating electrodes including the first passive electrode.

20. An ion-sensitive probe to measure the concentration of an ion within a solution, the ion-sensitive probe comprising: a semiconductor substrate; and a first passive electrode integrated with the semiconductor substrate and configured to contact the solution; a second passive electrode, integrated with the same semiconductor substrate and configured to contact a reference solution having a specified concentration of the ion; an amplifier circuit, integrated with the same semiconductor substrate, and connected to the first and second passive electrodes, wherein the amplifier circuit is configured to provide a first electrical voltage as function of the concentration of the ion within the solution, wherein a location of the amplifier integrated within the semiconductor substrate is configured to provide a co-integrated transmission path of the first voltage to reduce susceptibility of interference of the first voltage between the first electrode and the input of the amplifier.

* * * * *